United States Patent
Herman

(10) Patent No.: US 8,986,659 B2
(45) Date of Patent: Mar. 24, 2015

(54) DIAMOND, PRECIOUS AND SEMI-PRECIOUS DUST POLISHING AGENT FOR DENTAL VENEERS AND TEETH

(75) Inventor: Michael Herman, New York, NY (US)

(73) Assignee: Wam Oral Care Products, LLC, Aventura, FL (US)

( * ) Notice: Subject to any disclaimer, the term of this patent is extended or adjusted under 35 U.S.C. 154(b) by 104 days.

(21) Appl. No.: 12/288,708

(22) Filed: Oct. 22, 2008

(65) Prior Publication Data
US 2009/0130031 A1    May 21, 2009

Related U.S. Application Data

(60) Provisional application No. 61/003,552, filed on Nov. 16, 2007.

(51) Int. Cl.
| | | |
|---|---|---|
| *A61Q 11/00* | (2006.01) | |
| *A61K 8/06* | (2006.01) | |
| *A61K 8/02* | (2006.01) | |
| *A61K 8/19* | (2006.01) | |
| *A61K 6/00* | (2006.01) | |
| *B82Y 5/00* | (2011.01) | |

(52) U.S. Cl.
CPC . *A61Q 11/00* (2013.01); *A61K 8/19* (2013.01); *A61K 2800/28* (2013.01); *A61K 2800/413* (2013.01); *B82Y 5/00* (2013.01); *A61K 8/0241* (2013.01)
USPC ............................. 424/49; 424/401; 424/46

(58) Field of Classification Search
USPC ............... 106/288; 424/401, 49, 46
See application file for complete search history.

(56) References Cited

U.S. PATENT DOCUMENTS

| 4,021,263 | A | * | 5/1977 | Rosenblum | .................... | 106/474 |
| 6,033,582 | A | * | 3/2000 | Lee et al. | .......................... | 216/37 |
| 6,117,415 | A | * | 9/2000 | Schwarz | .......................... | 424/49 |
| 2005/0220829 | A1 | * | 10/2005 | Sung et al. | .................... | 424/401 |
| 2006/0130409 | A1 | * | 6/2006 | Chen | .............................. | 51/307 |
| 2006/0140881 | A1 | * | 6/2006 | Xu et al. | .......................... | 424/49 |

OTHER PUBLICATIONS

Yotis et al., Antimicrobial properties of testosterone and its intermediates, Antonie van Leeuwenhoek, 1968, 34, pp. 275-286.*
Updegraff et al., Antibacterial Activity of Dental Restorative Materials, Journal of Dental Research, 1971, 50(2), pp. 382-387.*
Humana. How to reduce dental plaque. https://www.humana.com/learning-center/health-and-wellbeing/healthy-living/dental-plaque.*
Silverson Machines Inc. Manufacture of Toothpaste. May 10, 2006. Application Report, Issue No. 57TAI. pp. 1-4.*

* cited by examiner

*Primary Examiner* — Frederick Krass
*Assistant Examiner* — Tracy Liu

(57) ABSTRACT

A diamond dust polishing agent for home use and professional use in the care of natural tooth enamel and dental veneers comprised of a quantity of diamond dust coated with a lubricant in conjunction with a paste for carrying the lubricant coated diamond dust, or other semi-precious, non-toxic abrasive dust, said diamond dust being of a size of approximately 500 nanometers or less to a size of approximately 5 nanometers. The size of the dust of both the diamond and the semi-precious stone may vary, depending on the degree of abrasiveness and the lubricant employed. The diamond dust (and semi-precious dust) polishing agent permits the user to maintain the polish and luster of the natural tooth enamel and veneer at home without adversely abrading or damaging the surface thereof.

9 Claims, No Drawings

DIAMOND, PRECIOUS AND SEMI-PRECIOUS DUST POLISHING AGENT FOR DENTAL VENEERS AND TEETH

This application claims the priority of Provisional Application No. 61/003,552 filed Nov. 16, 2007.

FIELD OF THE INVENTION

The present invention relates to the field of dental hygiene and cosmetics, particularly as applied to preservation of good facial appearance. The invention is directed to maintaining the luster of tooth enamel and dental veneer, prevention of discoloration of particularly the front tooth region by facilitating removal therefrom of common residual staining substances between regular brushings, promptly after exposure to such substances. The present invention also relates to a product and system for permitting both the professional and home polishing of natural tooth enamel and veneers that are applied to the teeth of individuals without the need to have the natural tooth enamel or veneers polished by a dentist in their office. The invention provides for the coating of a quantity of precious and/or semi-precious dust having an overall dimension of approximately 500 nanometers or less with an organic, or synthetic, non-toxic coating held thereon and the integration of the coated precious and/or semi-precious dust into a toothpaste emulsion.

BACKGROUND OF THE INVENTION

Facial appearance is of prime importance to most individuals, and is greatly enhanced by the appearance of clean white teeth. This applies both to natural tooth enamel and veneers. Conversely, facial appearance is greatly degraded by stain discoloration that develops over time from the cumulative effects of frequent and repeated exposures to staining substances, despite normal regular brushings.

Modern lifestyles, including increased public travel trends, have tended to intensify the exposure of many to teeth-staining substances such as nicotine, coffee and many other beverages and foods. Due to lack of convenient facilities, often the period between regular brushings can extend to as much as 16 hours or more. Consequently, especially for the appearance-conscious, there is an unfulfilled need for a convenient way to remove these unwanted residuals from at least the frontal areas of the teeth as promptly as possible after each of numerous incidents of daily exposures between regular brushings and to maintain the polish and luster of both natural tooth enamel and dental veneers.

There is a demand in the marketplace for a tooth whitening dentifrice that can be used at home by the consumer on both natural tooth enamel and dental veneers which is safe and easy to use.

Dental veneers have, for many years, been employed to enhance facial appearance and particularly the look and regularity of front teeth that are visible. Dental veneers (sometimes called porcelain veneers or dental porcelain laminates) are wafer-thin, custom-made shells of tooth-colored materials designed to cover the front surface of teeth to improve appearance. These shells are bonded to the front of the teeth changing their color, shape, size or length.

Dental veneers can be made from porcelain or from resin composite materials. Porcelain veneers resist stains better than resin veneers and better mimic the light reflecting properties of natural teeth. Resin veneers are thinner and require removal of less of the tooth surface before placement. Generally, the best choice of veneer material for is determined by the patient in consultation with their dentist.

Veneers are routinely used to fix:
  Teeth that are discolored—either because of root canal treatment; stains from tetracycline or other drugs, excessive fluoride or other causes; or the presence of large resin fillings that have discolored the tooth
  Teeth that are worn down
  Teeth that are chipped or broken
  Teeth that are misaligned, uneven, or irregularly shaped (for example, have craters or bulges in them)
  Teeth with gaps between them (to close the space between these teeth)

Generally to prepare a tooth for a veneer, a dentist will remove about ½ millimeter of enamel from the tooth surface, and then bond or otherwise adhere to the remaining surface of the tooth the veneer material.

Veneers offer the following advantages:
  They provide a natural tooth appearance.
  Gum tissue tolerates porcelain well.
  Porcelain veneers are stain resistant.
  The color of a porcelain veneer can be selected such that it makes dark teeth appear whiter.
  Veneers offer a conservative approach to changing a tooth's color and shape-veneers generally don't require the extensive shaping prior to the procedure that crowns do, yet offer a stronger, more aesthetic alternative to bonding.

The downside to dental veneers include:
  The process is not reversible.
  Veneers are more costly than composite resin bonding.
  Veneers are usually not repairable should they chip or crack.
  Because enamel has been removed, a tooth may become more sensitive to hot and cold foods and beverages.
  Veneers may not exactly match the color of one's other teeth. Also, the veneer's color generally cannot be altered once in place
  Though not likely, veneers can dislodge and fall off.
  Teeth with veneers can still experience decay, possibly necessitating full coverage of the tooth with a crown.

Veneers generally last between 5 and 10 years. After this time, the veneers would need to be replaced.

Even though porcelain veneers resist stains, certain stain-causing foods and beverages for example, coffee, tea or red wine, can discolor the veneer. Similarly, the surface of the veneer can become marred or otherwise not reflect light in a pleasing manner so that the appearance of the veneer needs to be restored by polishing.

All toothpastes help remove surface stains because they have mild abrasives. Some whitening toothpastes contain gentle polishing or chemical agents that provide additional stain removal effectiveness. Whitening toothpastes can help remove surface stains only and do not contain bleach; over-the-counter and professional whitening products contain hydrogen peroxide (a bleaching substance) that helps remove stains on the tooth surface as well as stains deep in the tooth. However, commerically available toothpastes do not contain any polishing agent that would permit a veneer surface to be polished to restore its original luster. A patient cannot polish the veneer surface at home or on a regular basis inasmuch as the current technology requires that such polishing be done by a dentist in their offices.

Diamond is the hardest material known and is commonly used as a superabrasive for removing excess materials. Diamond superabrasives have been commercially available in a number of mesh sizes. For example, diamond saws typically incorporate diamond particles having a U.S. mesh size of 18 (about 1 mm) to 60 (about 0.25 mm). Polishing applications typically require diamond fines down to about 0.1 micron. Until recently, diamond particles smaller than about 100 nm were not commercially available.

Diamond micron powders are commonly made by pulverizing waste diamond grains that are not otherwise suitable for ultrafine polishing where nanometer scale smoothness is desired. However, typical pulverized diamond particles may include sharp corners and irregular shapes which are not suitable for polishing of surfaces which require smoothness and luster to remain. Thus, they would generally be unsuitable for use as a tooth polish or veneer polish. Recently, nanoparticles of diamond have become commercially available. Such nanodiamond particles are commonly formed by explosion where the graphite is compressed with a shock wave and the dynamite (e.g. TNT and RDX mixture) itself is converted to nanodiamond during less than a microsecond at high pressure and temperature. Nanodiamonds so formed are typically smaller than 10 nm (e.g. 5 nm) and tend to have a very narrow size distribution, i.e. from about 4 nm to about 10 nm. More importantly, the surface of these nanodiamonds contains diamond or diamond-like carbon, such as bucky balls (C60), layered shells, carbon nanotubes, and amorphous carbon which makes these nanodiamonds extremely hard without sharp corners. Such nanodiamond has been used as abrasives for the ultra-fine polishing of hard materials (e.g. gems), but there has been no use of them to permit the polishing of natural tooth enamel or dental veneer.

Aggregated diamond nanorods, or ADNRs, are a nanocrystalline form of diamond. These are synonymous with the more conventional (and perhaps more justified) term "nanodiamond". Nanodiamond may be produced by compression of graphite and is much harder than bulk diamond, which makes it the hardest known material with an isothermal bulk modulus of 491 gigapascals (GPa). A conventional diamond has a modulus of 442-446 GPa. These results may be inferred from X-ray diffraction data, which also indicated that ADNRs are 0.3% denser than regular diamond. ADNRS can have a hardness and Young's modulus comparable to that of natural diamond, but with superior wear resistance.

SUMMARY OF THE INVENTION

The present invention encompasses a nanodiamond or semi-precious dust component dental whitening composition for home use which when applied to teeth contains a combination of a polishing diamond dust compound and carrier material whereby both heightened whitening and stain removal from teeth is attained.

The present invention is based upon the discovery that when a dentifrice component and an abrasive containing dentifrice component which abrasive is retained within the composition, are combined and applied to the surface of the teeth, an enhanced whitening effect is obtained, when the teeth are brushed, as a result of the combined presence of the carrier and abrasive ingredients.

In one embodiment of the invention, a dental whitening composition is provided which is comprised of diamond dust and a biological material or glycerin based carrier containing dentifrice components. The invention permits individuals to polish their natural teeth or their dental veneers on a regular basis, at home, without the assistance or intervention of a dentist.

A precious and/or semi-precious dust polishing agent comprised, by way of example only, of a quantity of diamond dust coated with a lubricant, generally adhered to the diamond dust by means of sonification or other bonding technique, is carried in suspension in a paste. The lubricant permits the dust to gently polish the natural tooth enamel or veneer, while preventing it from overly abrading the surface. The dust particles, before coating, are approximately 500 nanometers or less in size. The dust polishing agent permits the user to maintain the polish and luster of natural tooth enamel or dental veneer at home without adversely abrading or damaging the surface thereof.

By way of further example, the volume of the diamond dust in suspension may be varied, in accordance with an embodiment of the invention. One advantageous concentration of coated diamond dust, in relation to the volume of toothpaste, is approximately 15% of the overall volume of the mixture.

The coating material on the diamond dust may also be varied, in accordance with another embodiment of the invention. Glycerin or olive oil may be employed, as well as inorganic and synthetic materials, so long as they are non-toxic when applied and sufficiently coat individual particles of the diamond dust to produce a polishing effect and not abrade or degrade the veneer surface.

DETAILED DESCRIPTION OF THE INVENTION

Definitions

In describing and claiming the present invention, the following terminology will be used in accordance with the definitions set forth below.

The singular forms "a," "an," and "the" include plural referents unless the context clearly dictates otherwise. Thus, for example, reference to "a solvent" includes reference to one or more of such solvents, and reference to "the dispersant" includes reference to one or more of such dispersants.

As used herein, "formulation" and "composition" may be used interchangeably and refer to a combination of elements that is presented together for a given purpose. Such terms are well known to those of ordinary skill in the art.

As used herein, "carrier," "inert carrier," and "acceptable carrier" may be used interchangeably and refer to a carrier which may be combined with a plurality of nanodiamond particles in order to provide a desired composition. Those of ordinary skill in the art will recognize a number of carriers that are well known for making specific remedial healthcare and/or cosmetic compositions.

As used herein, "biologically acceptable carrier" refers to a material which is suitable for use in connection with a particular biological material. A biologically acceptable carrier is compatible with, and does not adversely affect, a biological material or subject contacted therewith under prescribed conditions.

As used herein, "cosmetic" is an adjective referring to improving the appearance of a surface or covering defects. Typically, cosmetic compositions can be used to improve aesthetic rather than functional aspects of a surface. Most commonly, cosmetic compositions are formulated for application as A beauty treatment or for affecting personal appearance of the body, for example, natural tooth enamel and dental veneer surfaces.

As used herein, "remedial" is an adjective referring to remedying, correcting, treating, improving, or preventing an undesirable condition. A remedial composition can therefore be formulated to remove undesirable stains from the surface of natural tooth enamel or veneer. Similarly, remedial compositions can be configured to remove, prevent or minimize formation of undesirable elements such as stain build up and the like.

As used herein, "biological material" refers to any material which is a product of a biological organism. Typical biological materials of interest can include organic oils and the like.

As used herein, "lubricating," when used in connection with nanodiamond contact with biological or non-biological materials, refers to the ability of a material to coat and adhere to the nanodiamond and permit the gentle polishing action without undo abrasion.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of 1 to 5 should be interpreted to include not only the explicitly recited limits of 1 and 5, but also to include individual values such as 2, 2.7, 3.6, 4.2, and sub-ranges such as 1-2.5, 1.8-3.2, 2.6-4.9, etc. This interpretation should apply regardless of the breadth of the range or the characteristic being described, and also applies to open-ended ranges reciting only one end point, such as "greater than 25," or "less than 10".

In the practice of the present invention, the dentifrice components in which the abrasive diamond dust material is included is generally prepared using a vehicle which contains water, humectant, surfactant and thickener.

The humectant is generally a mixture of humectants, such as glycerin, sorbitol and a polyethylene glycol of a molecular weight in the range of 200-1000, but other mixtures of humectants and single humectants may also be employed.

The humectant content is in the range of about 10% to about 80% by weight and preferably about 40 to about 50% by weight. The water content is in the range of about 10 to about 20% by weight.

Thickeners which may be used in the preparation of the abrasive component include natural and synthetic gums such as carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose. The thickener may be incorporated in the dentifrice composition of the present invention at a concentration of about 0.1 to about 3% by weight and preferably about 0.5 to about 1% by weight.

Surface active agents are incorporated in the diamond dust dentifrice to provide foaming properties. The surface-active material is preferably anionic, nonionic or ampholytic in nature, and most preferably is anionic. Suitable examples of useful anionic surfactants are higher alkyl sulfates such as potassium or sodium lauryl sulfate which is preferred, higher fatty acid monoglyceride monosulfates, such as the salt of the monosulfated monoglyceride or hydrogenated coconut oil fatty acids, alkyl aryl sulfonates such as sodium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the salts of N-lauroyl, N-myristoyl, or N-palmitoyl sarcosine. The surface active agent is generally present at a concentration of about 0.5 to about 5.0% by weight.

By way of for example, a humectant used herein is at least one or two substances selected from the group consisting of glycerine, sorbitol solution and amorphous sorbitol solution. Additives used in a small content are ordinary components used in the tooth paste and include sweetening agents, pH controlling agents, antiseptic substances, coloring agents and binders. The sweetening agents are sodium saccharide, aspartame, etc., the pH controlling agents are sodium phosphate, disodium phosphate, citric acid, etc., and the antiseptic substances are paraoxy benzoin methyl, sodium benzoin, etc.

The binders or thickeners may be selected from a number of variants including sodium carboxymethyl cellulose, carrageenan, xantan gum, etc. A foaming agent used herein may be anionic and non-ionic surfactants of sodium lauryl sulfate, saccharose carboxylic ester and sorbitan carboxylic ester in a sole form or in a combination of at least two thereof.

A flavouring agent used herein may be selected from a group including a mixture of peppermint oil, spearmint oil, menthol, etc., and other additives are enzymes such as dextranase, etc.

With regard to the cleaning material including the diamond dust, this is selected to effectively dissolve and remove residual material when used immediately after exposure to staining substances, without harmful abrasive action but with sufficient such action as to polish either natural tooth enamel or dental veneer, and to be of a neutral harmless composition that is totally harmless to ingest. The invention could be practiced with cleaning material in powder, liquid, paste or even in solidified form; preferably it may include a breath-freshener and/or distinctive pleasant flavoring. As an important marketing feature, the cleaning material can be formulated to also serve as a breath-freshener by the inclusion of suitable ingredients such as mint. Furthermore, the cleaning material can be formulated to provide a distinctive pleasant flavor, or offered in a variety of flavors, with or without the breath-freshening feature.

It can be appreciated that there is a broad range of dust sizes as well as overall concentrations. By way of example only, the following concentrations and procedures may be employed:

Examples 1 Through 3

|  | Toothpaste containing: | | |
| --- | --- | --- | --- |
| Ingredients | 0.5 CT/4 oz % w/w | 0.0125 CT/4 oz % w/w | 12.5 CT/4 oz % w/w |
| Diamond dust in Glycerin, 1 CT/g | 0.40 | .0/1 | 10.00 |
| Carrageenan | 0.60 | 0.60 | 0.60 |
| Sorbitol Solution | 24.00 | 24.00 | 24.00 |
| Glycerin | 22.00 | 22.00 | 14.00 |
| Purified Water | 16.00 | 16.39 | 16.00 |
| Calcium Carbonate | 35.00 | 35.00 | 35.00 |
| Sodium Saccharin | 0.20 | 0.20 | 0.20 |
| Peppermint Oil | 0.80 | 0.80 | 0.80 |
| Sodium Lauryl Sulfate | 1.00 | 1.00 | 1.00 |

Procedure:
1. Disperse Carrageenan into Glycerin and Sorbitol solution with high speed mixing.
2. Add water and continue mixing to a thick gel.
3. Dissolve sodium saccharin, then add Diamond Dust in Glycerin and calcium carbonate, mix well under vacuum.

4. Add peppermint oil and sodium lauryl sulfate and mix under vacuum.

Example 4

Dental gel containing 0.5 CT/4 oz

| Ingredients | % w/w |
|---|---|
| Diamond dust in Glycerin, 1 CT/g | 0.40 |
| Cellulose gum | 0.40 |
| Glycerin | 8.00 |
| Sorbitol Solution | 52.00 |
| Purified Water | 15.00 |
| Carbowax 600 | 2.00 |
| Sodium Benzoate | 0.30 |
| Hydrated Silica | 0.20 |
| Sodium Saccharin | 0.20 |
| Flavor | 1.00 |
| Sodium Lauryl Sulfate | 0.70 |

Procedure:
1. Combine water, glycerin and sorbitol solution and disperse cellulose gum with mixing until thoroughly.
2. Add Carbowax 600 and heat to 50° C.
3. Dissolve sodium benzoate and sodium saccharin
4. Add Diamond Dust in Glycerin and mix well, cool to 25-30° C.
5. Add hydrated silica, flavor and sodium lauryl sulfate. Mix well under vacuum.

Example 5

| Ingredients | % w/w |
|---|---|
| Viscarin TP 399 | 0.700 |
| Glyerin 99% Natural USP | 26.499 |
| Purified Water USP | 16.500 |
| Xylitol | 8.250 |
| Whole Leaf Aloe 5X | 0.100 |
| Stevia Extract | 0.150 |
| Sodium Bicarbonate USP | 1.200 |
| Ubidencarenone NF | 0.001 |
| Diamond dust in Glycerin | 0.400 |
| Titanium Dioxide USP | 1.000 |
| VICALity Heavy PCC | 33.00 |
| Zeodent 113 | 10.50 |
| Natural Peppermint Oil (Chinese redistilled) | 0.430 |
| Natural Spearmint Oil (Chinese) | 0.370 |
| Sodium Lauryl Sulfate USP | 0.900 |

Procedure:
1. Disperse Viscarin into glycerin with high speed mixing. Stir for 5 minutes.
2. Add water and continue mixing for 15 minutes more.
3. Add Aloe with agitation, then add and dissolve xylitol, stevia extract, sodium bicarbonate and ubidencarenone.
4. Add diamond dust in glycerin and transfer gel to a Ross type mixer.
5. Add under vacuum titanium dioxide, Zeodent 113 and calcium carbonate. Mix well under vacuum.
6. Add flavors, mix under vacuum.
7. Add sodium lauryl sulfate and mix under vacuum.

Other ingredients which may be incorporated in the present invention include pigment, sweetener, flavor and preservative. In white dental cream formulations, the pigment will be titanium dioxide, rutile, and the proportion thereof will normally be in the range of 0.5 to 1% by weight, preferably 0.75 to 1.25% by weight. The sweetener content will normally be that of an artificial or synthetic sweetener and the normal proportion thereof present will be in the range of 0.1 to 1% by weight, preferably 0.1 to 0.5% by weight. The flavor content, which is preferably of a mixed peppermint/menthol flavor, will usually be in the range of 0.5 to 2% by weight, preferably 0.5 to 1.5% by weight. F.D. & C grade dyes may be used in appropriate amounts to provide desired colors.

Additional ingredients which may be incorporated in the present invention are antibacterial agents including noncationic antibacterial agents such as halogenated diphenyl ethers such as 2',4,4'-trichloro-2-hydroxy-diphenyl ether (Triclosan) and phenolic compounds including phenols, and their homologs, mono- and polyalkyl and aromatic halophenols, resorcinol and its derivatives, bisphenolic compounds and halogenated salicylanilides. Examples of other antibacterial agents which may be included in tooth paste include chlorhexidine, copper- and zinc-salts such as zinc citrate and sodium zinc citrate, sanguinarine extract, and metronidazole, quaternary ammonium compounds such as cetylpyridinium chloride, bis-guanides such as chlorhexidine digluconate, hexetidine, octenidine and alexidine.

An antibacterial agent may also be present in an effective antiplaque amount, typically 0.01-5% by weight, preferably about 0.03 to about 1% by weight.

Anti-inflammatory agents such as ibuprofen, flurbiprofen, aspirin, indomethacin etc. may also be included.

An anticalculus agent which is effective against calculus such as pyrophosphate salts including the mono, di, tri and tetra alkali metal and ammonium pyrophosphate and tripolyphosphate salts is still another additional ingredient which may be present in the abrasive component of the present invention. Such agents are used in amounts sufficient to reduce calculus and are preferably in amounts which will release about 1% by weight $P_2O_7$ ion and most preferably at least about 1.3% by weight $P_2O_7$ ion.

Plaque buffers such as calcium lactate, calcium glycerophosphate and stronthium polyacrylates may also be included in the abrasive component. Other optional ingredients include vitamins such as vitamin A, C, E, $B_6$, $B_{12}$, K, plant extracts as well as potassium salts useful in the treatment of dentin hypersensitivity such as potassium citrate, potassium chloride, potassium sulfate, potassium tartrate and potassium nitrate.

The toothpaste provided by this invention can also contain, if so desired, a vitamin selected from the group formed by vitamin A, vitamin B5, vitamin C, vitamin E, and mixtures thereof. If they are used each vitamin can be present in the formulation at a quantity lying between 0.1 and 5% by weight with respect to the total. These vitamins can be used as they are, in the form of pro-vitamins or in the form of pharmaceutically acceptable salts. Vitamin A, which is usually used in the form of palmitate salt, promotes the epithelialisation of oral mucus and protects the gums. Vitamin B5, more specifically D-pantenol, has a soothing, curative, anti-inflammatory effect on epithelial lesions, promotes the epithelialisation of injuries and softens scar tissue, and is suitable for the treatment of injuries produced as a consequence of dental extractions, gingivitis, stomatitis, pain produced by putting false teeth in place, ulcers, traumatic lesions of the mucus and chronic and recurrent cankers. Vitamin C regenerates the epithelium of the oral mucus, stimulates the synthesis of collagen and the immune system (inflammation mechanism) and increases the capacity for protection of the phagocyte cells against bacteria. Vitamin E, which is usually used in the form of acetate salt, has a calming and anti-inflammatory effect, protects oral mucus against lipid peroxidation due to the formation of free radicals and against environmental contaminants (ozone, cigarette smoke, etc.) and favours the healing of injuries. By the incorporation of all or some of the aforementioned vitamins, the invention provides toothpastes that, as well as the aforementioned characteristics, have anti-inflammatory properties and are effective soothing agents, and that increase the protective properties of the membranes of the oral mucus, reduce the occurrence of plaque and gingival as well as bacterial contamination.

The toothpaste may also contain, if desired, human pheromones, including androstadienone (delta 4,16-androstadien-3-one) (AND) and estratetraenol (EST). AND is a derivative of testosterone and EST is a relative of estrogen. Other human pheromones which may be included are androstenone, androstenol, androsterone, copulins and androstadienol. Musk may also be added.

Although the description of the invention identifies natural tooth enamel and tooth veneer as a primary beneficiary of the invention, it is not limited thereto. It is applicable to other surface materials and methodologies to permit the patient to achieve the original luster and appearance of the treated natural or veneer tooth surface. Those skilled in the art will recognize that there exist a substantial number of variations that could be used in conjunction with one or more aspects of the invention and that the invention could be implemented with different size dust particles of precious and/or semi-precious stones and coatings. While the above is a description of specific embodiments of the invention, numerous additional embodiments are possible. Moreover, various aspects of the invention may be modified, combined, taken in varying order, added to or taken out without departing from the spirit and breadth of the invention. Similar pathways and equivalent means and steps may be employed within the scope of the inventive concept. Therefore, the above descriptions should not be taken as in any way limiting the scope of invention.

It is to be understood that the above-described compositions and methods are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in materials, temperature, function, order, and manner of operation, assembly and use may be made without departing from the principles and concepts set forth herein.

What is claimed is:

1. A diamond dust polishing agent toothpaste emulsion for home and professional application in the oral cavity by brushing in the care of natural tooth enamel and applied non-metal dental veneers comprising:
   a. a quantity of diamond dust;
   b. a lubricant which coats and adheres to the diamond dust, said lubricant having been applied to said diamond dust under vacuum prior to integration into the toothpaste emulsion to cause the lubricant to coat and adhere to the diamond dust; and,
   c. a paste for carrying the lubricant coated and adhered diamond dust which forms a toothpaste emulsion applied in the oral cavity by brushing, said diamond dust being of a size of approximately 500 nanometers or less to a size of approximately 5 nanometers.

2. A diamond dust polishing agent toothpaste emulsion in accordance with claim 1 wherein the lubricant comprises from about 10% to about 80% by weight of the emulsion.

3. A diamond dust polishing agent toothpaste emulsion in accordance with claim 1 wherein the lubricant is a humectant.

4. A diamond dust polishing agent toothpaste emulsion in accordance with claim 3 wherein the humectant is selected from the group consisting of glycerine, sorbitol solution, amorphous sorbitol solution and mixtures thereof.

5. A diamond dust polishing agent toothpaste emulsion in accordance with claim 1 wherein the diamond dust comprises from about 0.1% to about 40% by weight of the polishing agent emulsion.

6. A diamond dust polishing agent toothpaste emulsion in accordance with claim 1 wherein the diamond dust particles are without sharp corners.

7. A diamond dust polishing agent toothpaste emulsion in accordance with claim 6 comprising nanodiamonds containing on their surface diamond-like carbon selected from the group consisting of bucky balls (C60), layered shells, carbon nanotubes, amorphous carbon and mixtures thereof.

8. A diamond dust polishing agent toothpaste emulsion in accordance with claim 1 further comprising a human pheromone.

9. A diamond dust polishing agent toothpaste emulsion in accordance with claim 8 wherein the human pheromone is selected from the group consisting of androstadienone (delta 4,16-androstadien-3-one), androstenone, androstenol, androsterone, copulins, androstadienol, musk and mixtures thereof.

* * * * *